United States Patent [19]

Whitesides et al.

[11] 4,411,995
[45] Oct. 25, 1983

[54] SYNTHESIS OF NICOTINAMIDE COFACTORS

[75] Inventors: George Whitesides, Newton; Davis R. Walt, Brookline, both of Mass.

[73] Assignee: Massachusetts Institute of Technology, Cambridge, Mass.

[21] Appl. No.: 306,460

[22] Filed: Sep. 28, 1981

[51] Int. Cl.³ .................... C12P 19/36; C12N 11/08; C07H 15/12; C07H 19/00

[52] U.S. Cl. ........................................ 435/90; 435/89; 435/177; 435/180; 536/26; 536/27

[58] Field of Search ................... 435/89, 90, 174, 177, 435/180, 182; 536/22, 26, 27, 23, 29

[56] References Cited

PUBLICATIONS

Walt, et al., Synthesis of Nicotinamide Adenine Dinucleotide (NAD) from Adanosine Monophosphate (AMP), J. Am. Chem. Soc., vol. 102, 1980 (pp. 7805–7806).

Tipson, R. S., Acetylation of D–Ribosylamine, J. Org. Chem., vol. 26, 1961 (pp. 2462–2464).

*Primary Examiner*—David M. Naff
*Attorney, Agent, or Firm*—Arthur A. Smith, Jr.; Thomas J. Engellenner

[57] ABSTRACT

Nicotinamide cofactors are prepared in a process of reacting ribose -5- phosphate with a basic material selected from the group consisting of ammonia, primary and secondary amines in a polar non-aqueous solvent, reacting the resultant 1-ribosylamine -5- phosphate with a pyridinium salt and reacting the resultant nicotinamide mononucleotide with adenosine triphosphate in the presence of nicotinamide adenine dinucleotide pyrophosphorase to produce nicotinamide adenine dinucleotide which can be used directly in crude form without further purification in co-factor - requiring enzymatic reactions. The nicotinamide adenine dinucleotide pyrophosphorase may be immobilized on a solid support.

11 Claims, No Drawings

SYNTHESIS OF NICOTINAMIDE COFACTORS

The U.S. Government has rights in this invention pursuant to a grant from the National Institute of Health No.: NIH-5-R01-GM26543-02.

TECHNICAL FIELD

The field of this invention is organic chemical synthesis and, more particularly, synthesis of cofactors for enzymatic oxidation and reduction.

BACKGROUND ART

The acceptance of enzyme catalyzed oxidation and reduction reactions in organic synthesis has been slowed by the expense of the nicotinamide cofactors required by many of these enzymes.

Nicotinamide Adenine Dinucleotide (NAD), for example, is a cofactor which is useful in a variety of enzyme catalyzed reactions, such as producing optically active alcohols, synthesizing carbohydrates, synthesizing fine chemicals, producing aldehydes and carboxylic acids, functionalizing hydrocarbons, and producing amino acids.

NAD is manufactured almost exclusively by a process involving the fermentation of yeast. It presently requires approximately 1 lb. of yeast to manufacture one gram of NAD. The cost of manufacturing is approximately $1.60 per gram.

A typical industrial fermentation process for NAD is described in Kornberg in Vol. 3 of *Methods of Enzymology* pgs. 876-879 (1957). In the Kornberg fermentation process starch-free bakers yeast is dissolved in boiling water. After removal of other substances from the extract by basic lead acetate, silver nitrate is added and the preparation is allowed to settle over night. The precipitate is collected and decomposed with hydrogen sulfide. The NAD is obtained as the free acid by precipitation with acetone. Further purification is achieved by anion exchange chromatography.

NAD can also be synthesized from nicotinamide mononucleotide (NMN). However, NMN is a very difficult intermediate to obtain. For this reason non-fermentation processes for NAD have been uncompetitive. The conventional method for synthesizing NMN was reported by Jeck in Vol. 42 of the *Federation of European Biochemists Society Letters* pg. 161 (1974). The basic problem with NMN synthesis is that it must be derived from a beta-ribofuranose moiety. In the conventional synthesis techniques, as reported by Jeck article, various protecting groups were necessary to hold the ribose moiety in the furanose form. Moreover, in the Jeck technique, it is necessary to phosphorylate the beta-nicotinamide riboside as a final step in converting it into NMN. This addition of a phosphate group is a difficult procedure and the overall yields of NMN are quite low.

Additionally, the Jeck technique does not produce ribosylamine-5-phosphate (rA-5-P) as a chemical intermediate. Such an intermediate, itself, would also be valuable. rA-5-P and other 1-amino sugar phosphates can be used in principle to produce a variety of antibiotic and antiviral agents. For example, rA-5-P can be used in the manufacture of ribavirin, an antiviral agent of similar chemical structure.

Attention is directed to an article by the inventors and their colleagues entitled "Synthesis of Nicotinamide Adenine Dinucleotide (NAD) from Adenosine Monophosphate (AMP)" published in Vol. 102 of the *Journal of the American Chemical Society*, pgs. 7805-7806 (Dec. 17, 1980) and the references cited therein, all of which is hereby incorporated by reference.

There exist a need for a practical non-fermentation route to manufacture nicotinamide cofactors such as NAD, dihydro NAD (NADH), NAD phosphate (NADP) and dihydro NAP phosphate (NADPH). Moreover, there exist a need for more efficient methods of producing 1-amino sugar phosphates.

SUMMARY OF THE INVENTION

It has been discovered that NAD can be derived from relatively simple starting materials such as adenosine monophosphate (AMP) or ribose-5-phosphate (r-5-P) by a sequence of nonfermentation reactions using chemical and enzyme catalyzed steps. The sequence can be conducted in a single vessel and the final crude NAD is suitable for use in NAD-requiring organic synthesis without purification. Portions of the sequence also have general application in the preparation of 1-amino sugar phosphates and the wide class of compounds which can be derived therefrom. Moreover, the enzymatic steps are accomplished with ATP-cofactor recycling, greatly reducing the expense of the enzyme-catalysts.

In one aspect, our discovery permits the preparation of nicotinamide mononucleotide (NMN), a key intermediate in the NAD synthesis, without the need for protective-groups often required to generate products having the furanose configuration. Nicotinamide Mononucleotide (NMN) is produced from 1-ribosylamine-5-phosphate by condensation with an appropriate salt, such as N1-(2,4-dinitrophenyl)-3-carbamoylpyridinium chloride (NDC). By condensing NMN from an already phosphorylated ribosylamine, the difficulty typically encountered in selective phosphorylation of the primary hydroxyl group is also avoided.

In another aspect of our discovery ribosylamine-5-phosphate, used to produce NMN, is synthesized in a novel manner from Adenosine Monophosphate (AMP) or, alternatively, from ribose-5-phosphate. When starting from AMP, stoichometric amounts of AMP are converted to ribose-5-phosphate by acid catalyzed hydrolysis. Once the ribose-5-phosphate (r-5-P) is obtained, it is converted to ribosylamine-5-phosphate (rA-5P) by treatment with anhydrous ammonia in a dry solvent such as a polyhydric alcohol. It should be apparent that the rA-5P produced in this manner can find other applications, such as in the production of ribavirin and other antibiotic and antiviral agents.

The production of NAD from NMN is achieved in a unique manner by coupling the NMN to ATP in a step catalyzed by NAD pyrophosphorylase (NADPP) immobilized in a polyacrylamide (PAN) gel. See generally Pollak, "Enzyme Immobilization by Condensation Copolymerization into Cross-linked Polyacrylamide Gels" Vol. 102 *Journal of the American Chemical Society* pgs. 6324-6336 (1980) for a description of PAN gels. The enzymatic coupling of NMN was driven to completion by hydrolyzing the pyrophosphate (PPi) formed using pyrophosphorylase (PPase) in PAN. The yield of NAD was 90-97% based on NMN. It should be noted other enzyme immobilization techniques, besides the PAN gel technique, can be used to produce NAD from NMN.

The NAD produced was converted to NAD phosphate (NADP) by treating the product with NAD kinase (NADK), which was also immobilized, and ATP.

Both NAD and NADP can be converted to their reduced forms, NADH and NADPH, respectively, using standard techniques and reducing agents.

Another aspect of our invention that should be noted is the use of coupled ATP cofactor recycling throughout the synthesis. Since ATP is consumed in driving the reaction to NAD, additional ATP must be added or regenerated. Coupled ATP recycling avoids waste of adenosine moieties and reduces the overall expense since ATP is a costly reactant. Recycling is accomplished by adding only a catalytic amount of ATP and converting a stoichometric amount of AMP to ATP by reaction with acetyl phosphate (AcP) in the presence of acetyl kinase (AcK) and adenylate kinase (AdK). Even though the ATP is hydrolyzed in converting NMN to NAD, the recycling permits the regeneration of ATP. We note that other recycling and phosphorylation techniques (phosphoenol pyruvate/pyruvate kinase; carbamyl phosphate/carbamate kinase) can also be used to generate ATP from AMP or ADP in this synthesis:

The entire reaction can be illustrated as follows:

was removed (first using a rotary evaporator, and then a vacuum pump). NDC (162 g, 0.5 mol, in 250 mL of methanol) was added as a slurry, and the reaction mixture stirred in the dark for 18 h at 25° C. Water (1.5 L) was added, and precipitated 2,4-dinitroaniline removed by filtration. Excess NDC was removed by adsorption on activated charcoal (Darco, 25 g) and filtration. The resulting solution contained 125 mmol of β-NMN by enzymatic assay.

Alternatively, β-NMN was obtained as follows: Ethylene glycol (125 ml), dried over 3 Å molecular sieves was added to a 500 ml round bottomed flask with a magnetic stirrer. The flask was sealed with a rubber septum and cooled to 0° C. in an ice bath. Anhydrous ammonia was bubbled through the magnetically stirred ethylene glycol until bubbling in and out of solution were equal. Disodium ribose-5-phosphate (5 grams, 81% pure, 4.8 mmol) was added and the flask quickly resealed. Anhydrous ammonia was bubbled through the solution for an additional 15 minutes during which time the r-5-P dissolved. The solution was stored at 5° C. for

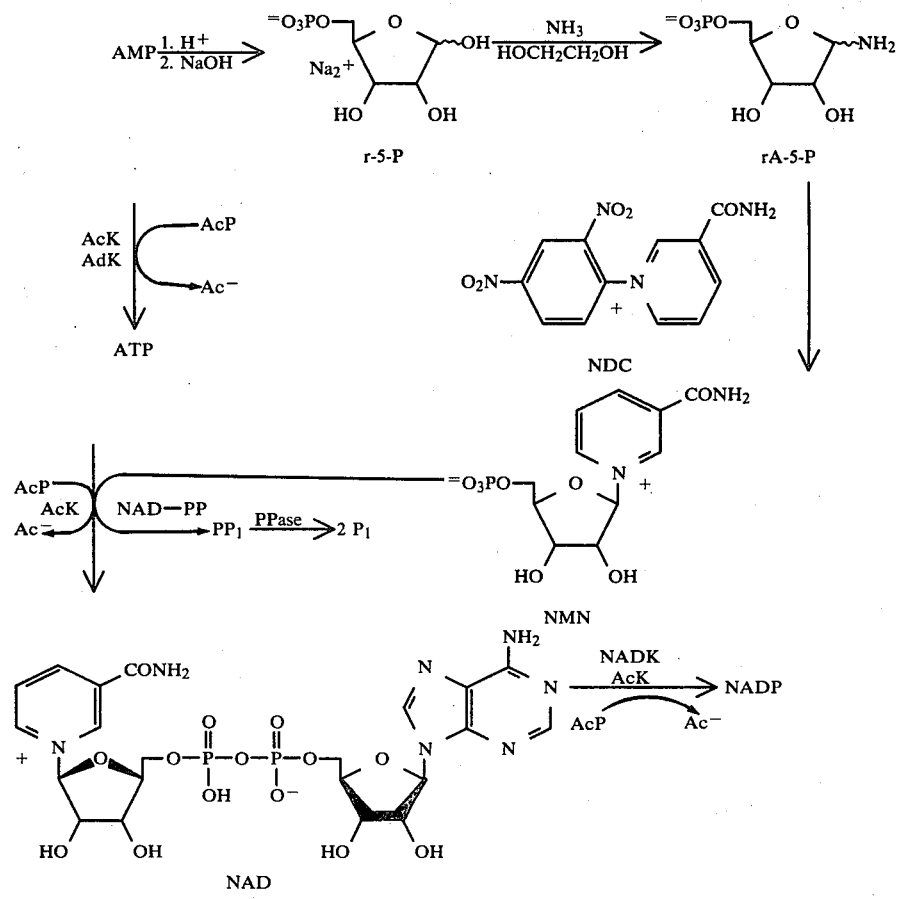

DESCRIPTION OF THE PREFERRED EMBODIMENT

The invention is best described with reference to the following, non-limiting, examples.

Disodium ribose-5-phosphate (156 g, 88% pure, 500 mmol) was dissolved in ethylene glycol (780 mL, dried over 3 A Molecular Sieves). The solution was cooled to 0° C., and anhyd. NH₃ was bubbled through it for 1 h. The yellow reaction mixture was stoppered and stored for 1 week in the refrigerator at 4° C. Excess ammonia 15 hours. Ammonia was removed with a vacuum pump for six hours while the flask was maintained at 0° C. in an ice bath. A cold solution of NDC (13.8 grams, 43 mmol) in anhydrous methanol (75 ml) was added to the solution of rA-5-P. The reaction mixture immediately turned deep red. The flask was sealed, wrapped in aluminum foil and stirred at 5° C. for 14 hours. The reaction mixture was then assayed by diluting an aliquot of solution with two volumes of 0.6 Molar HEPES buffer (7.4 pH) and centrifuged. Dinitroaniline and excess NDC were precipitated and the clear, pale, yellow solution subjected to enzymatic assay. The solution assayed for 8.85 mmol of β-NMN corresponding to a sixty percent yield.

For the enzymatic coupling, a 5-L flask was charged with 20 mmol of NMN, 25 mmol of AMP, 2 mmol of ATP, and 100 mL of PAN gel containing coimmobilized NAD-PP (50 U), PPase (50 U), AcK (100 U), and AdK (100 U). The reaction was adjusted to a volume of 2 L with distilled water, and the pH adjusted to 7.2. Magnesium chloride (50 mmol) and 1,3-dimercapto-2-propanol (20 mmol, protein antioxidant) were added, and the reaction blanketed with argon. Diammonium acetyl phosphate solution (AcP, 1 M, pH 7.0, stored at 0° C.) was added with stirring by peristaltic pump to maintain an ATP concentration above $K_m$ for NAD-PP (0.5 mM). Additional NMN (20 mmol) and AMP (25 mmol) were added over 10 days. At the conclusion of the reaction, 100 mmol of AcP had been added, and 39 mmol of NAD produced (97% based on NMN). The enzyme-containing gel was allowed to settle, and the reaction mixture decanted. A repetition of the reaction on the same scale and using the same enzymes consumed 110 mmol of AcP, and generated 37 mmol of NAD (91% based on NMN).

The solutions containing NAD could be used directly, without further purification, to provide NAD (or NADH) for cofactor-requiring enzymatic synthesis. Treatment of this crude NAD-containing solution with NAD kinase and ATP (using the ATP regeneration system) also generated NADP uneventfully. Thus, whatever the impurities present in the unpurified NAD may be, they do not appear to inhibit or inactivate other enzymes. If desired, however, solid NAD can be obtained in greater than 50% purity by acidifying the solution with Dowex 50 (H+ form), precipitating impurities with Ba(OH)$_2$, and precipitating NAD+ with ethanol.

In summary, our invention has several interesting features. First, this synthesis of NAD from readily available starting materials involves only one isolation (of r-5-P when AMP is used as the starting material: this isolation is required only to dry the r-5-P, and is straightforward). For all other steps, unpurified reaction mixtures are used directly, and enzymatic selectivity is used to direct reactants efficiently to products. Isolations and separations of nucleotides are laborious: a synthesis which requires only one simple separation has an advantage in convenience. Second, the NAD produced appears to be suitable for use in cofactor recycling procedures without further purification. Third, all of the enzymes required for the synthesis are easily immobilized and very stable: the manipulation of the enzymatic catalysts is thus straightforward. Finally, we note that the facile synthesis of rA-5-P should find application in other areas of nucleotide chemistry; that the use of r-5-P as starting material avoids many of the problems encountered in more extensively developed synthetic routes to nucleotides, by avoiding the protecting groups often required to generate a product having the furanose configuration; and that preliminary studies suggest that NAD-PP has sufficiently broad specificity to catalyze the coupling of NMN and ATP moieties bearing at least some structural modifications.

It should be obvious to those skilled in the art that various changes and modifications can be made in our process without departing from the spirit and scope of our invention. For example, sugars, other than ribose, can be employed in our process to produce other 1-amino sugar phosphates. A variety of pyridinium salts, such as nitro (or dinitro or trinitro) benzyl carbamoyl pyridinium chloride, or similar nitro-aromatic, acetyl or alkoxycarbonyl, pyridinium salts, can be used in place of NDC to produce NMN by condensation. Likewise a variety of polyhydric alcohols can be substituted for the ethylene glycol to dissolve r-5-P and the ammonia-reaction can be accomplished in a shorter time period (primary and secondary amines appear to be suitable substitutes for ammonia in the preparation of some 1-amino sugar phosphates).

What we claim is:

1. A method of preparing nicotinamide mononucleotide comprising the steps of
   (a) reacting ribose-5-phosphate with a basic material selected from the group of ammonia, primary and secondary amines and mixtures thereof in a polar, non-aqueous solvent solution; and
   (b) reacting the resulting product with a pyridinium salt having the following formula:

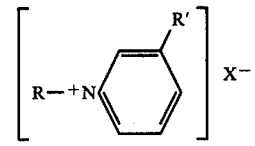

where R is a nitroaromatic group, R' is a carbamoyl, alkyl, acetyl or alkoxycarbonyl group and X is a halide or other anion for charge balance.

2. The method of claim 1 wherein the basic material is ammonia, the solvent is ethylene glycol and the salt is N1-2,4-dinitrophenyl-3-carbamoyl pyridinium chloride.

3. A method of preparing nicotinamide adenine dinucleotide comprising the steps of:
   (a) reacting ribose-5-phosphates with a basic material selected from the group of ammonia, primary and secondary amines and mixtures thereof while in a polar, non-aqueous solution;
   (b) reacting the resulting product with a pyridinium salt having the following formula:

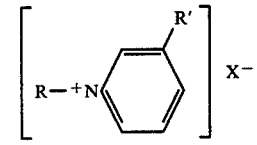

where R is a nitroaromatic group, R' is a carbamoyl, alkyl, acetyl or alkoxycarbonyl group and X is a halide or other anion for charge balance; and
   (c) reacting the second resulting product with adenosine triphosphate in the presence of nicotinamide adenine dinucleotide pyrophosphorase.

4. The method of claim 3 wherein the step of reacting the resulting product with adenosine triphosphate further comprises immobilizing the nicotinamide adenine dinucleotide pyrophosphorase on a solid support.

5. The method of claim 4 wherein the step of immobilizing the nicotinamide adenine dinucleotide pyrophosphorase further comprises immobilizing the nicotinamide adenine dinucleotide pyrophosphorase on a polyacrylamide gel.

6. The method of claim 3 wherein the method further comprising driving the reaction to completion by hydrolyzing pyrophosphate as it is formed.

7. The method of claim 6 wherein the step of hydrolyzing pyrophosphate further comprises hydrolyzing pyrophosphate with pyrophosphatase immobilized on a solid support.

8. The method of claim 3 wherein the step of reacting the resulting product with adenosine triphosphate further comprises aiding the reaction by the addition of adenosine or adenosine monophosphate and by enzymatic generation and regeneration of adenosine triphosphate from adenosine monophosphate or adenosine.

9. The method of claim 8 wherein the step of aiding the reaction further comprises using adenosine kinase to phosphorylate adenosine into adenosine monophosphate.

10. The method of claim 8 where the step of aiding the reaction further comprises using adenylate enzyme kinase to phosphorylate adenosine monophosphate into adenosine diphosphate.

11. The method of claim 8 wherein the step of aiding the reaction further comprises using acetate kinase to phosphorylate adenosine diphosphate to adenosine triphosphate.

* * * * *